US011369274B2

(12) United States Patent
Anderson et al.

(10) Patent No.: US 11,369,274 B2
(45) Date of Patent: Jun. 28, 2022

(54) METHOD AND DEVICE FOR VERIFICATION OF INTRA-LUMINAL PLACEMENT AND PATENCY FOR VASCULAR ACCESS DEVICES

(71) Applicant: Becton, Dickinson and Company, Franklin Lakes, NJ (US)

(72) Inventors: Robert John Anderson, Rochester, MN (US); Eric Michael Dinges, Edina, MN (US); Han Jun Kim, Sunnyvale, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 777 days.

(21) Appl. No.: 16/185,959

(22) Filed: Nov. 9, 2018

(65) Prior Publication Data
US 2020/0390340 A1 Dec. 17, 2020

Related U.S. Application Data

(60) Provisional application No. 62/584,496, filed on Nov. 10, 2017.

(51) Int. Cl.
*A61B 5/02* (2006.01)
*A61B 5/0215* (2006.01)
(Continued)

(52) U.S. Cl.
CPC ........ *A61B 5/02007* (2013.01); *A61B 5/0215* (2013.01); *A61B 5/065* (2013.01);
(Continued)

(58) Field of Classification Search
CPC ........ A61B 17/3403; A61B 2562/0233; A61B 2562/0247; A61B 5/02007; A61B 5/0215;
(Continued)

(56) References Cited

U.S. PATENT DOCUMENTS 4,576,181 A 3/1986 Wallace et al.
4,658,829 A 4/1987 Wallace
(Continued)

FOREIGN PATENT DOCUMENTS

WO 2017123764 A1 7/2017

OTHER PUBLICATIONS

"Pressure Transducers", http://www.utahmedicalproducts.com/oemdpt.htm, Utah Medical Products, Inc, downloaded Nov. 8, 2017.
(Continued)

*Primary Examiner* — Deanna K Hall
(74) *Attorney, Agent, or Firm* — Rutan & Tucker LLP

(57) ABSTRACT

Methods, apparatus, and systems to non-invasively determine intra-luminal placement and patency of a vascular access device. In one form, our device itself remains non-invasive, connecting at the vascular access device's hub outside the patient's body. Patency and/or placement are estimated indirectly by measuring a physiological parameter which is indicative of proper patency and/or placement of the vascular access device in a patient. The measurement is compared to a reference value or calibration. If the comparison indicates indication of proper patency and/or placement, a signal is generated. The signal can be used in a number of ways. One example is to give a user-perceivable alarm or indication of proper patency and/or placement. Non-limiting examples include activating a light, an audible buzzer, a vibration, readable displayed text or graphics, or some combination of the same. The user can then have an indirect and at least semi-automatic way of estimating proper patency and/or placement of a vascular access device. In one aspect of the invention, the technique is able to achieve this end by monitoring and detecting changes in the physiological parameter of systemic vascular pressure via pressure measurement in, at, or near the hub or other portion
(Continued)

of a vascular access device that has a lumen placed intraluminally, and then using the results of that monitoring to indirectly transduce conditions or states indicative of either good placement/patency or bad placement/patency of the vascular access device.

11 Claims, 12 Drawing Sheets

(51) Int. Cl.
*A61M 25/06* (2006.01)
*A61B 17/34* (2006.01)
*A61B 5/1455* (2006.01)
*A61B 5/00* (2006.01)
*A61M 39/02* (2006.01)
*A61B 5/06* (2006.01)
*A61M 25/00* (2006.01)
*A61B 5/1459* (2006.01)

(52) U.S. Cl.
CPC ........ *A61B 5/14552* (2013.01); *A61B 5/6852* (2013.01); *A61B 5/743* (2013.01); *A61B 5/7405* (2013.01); *A61B 5/746* (2013.01); *A61B 17/3403* (2013.01); *A61M 25/06* (2013.01); *A61M 39/0247* (2013.01); *A61B 5/1459* (2013.01); *A61B 2562/0233* (2013.01); *A61B 2562/0247* (2013.01); *A61B 2562/221* (2013.01); *A61M 25/003* (2013.01); *A61M 2025/0004* (2013.01); *A61M 2025/0681* (2013.01); *A61M 2039/0267* (2013.01)

(58) Field of Classification Search
CPC ..... A61B 5/02152; A61B 5/065; A61B 5/743; A61B 5/746
See application file for complete search history.

(56) References Cited

U.S. PATENT DOCUMENTS

| | | |
|---|---|---|
| 6,117,086 A | 9/2000 | Shulze |
| 10,687,781 B2* | 6/2020 | Navratil ............... A61B 5/7425 |
| 2016/0045715 A1 | 2/2016 | Galgano et al. |
| 2017/0196478 A1* | 7/2017 | Hunter ................ A61B 5/6847 |

OTHER PUBLICATIONS

Porth et al., Abstract, "The Valsalva maneuver: mechanisms and clinical implications", US National Library of Medicine, Heart Lung, vol. 13(5), pp. 507-518, Sep. 1984.
"Closed Needleless Arterial Blood Collection System", http://www.utahmedicalproducts.com/oemdpt.htm, Deltran® Technology for Critical Care, Utah Medical Products, Inc, Pub No. 5831, Rev. 102204, 8 pages, downloaded Nov. 8, 2017.

* cited by examiner

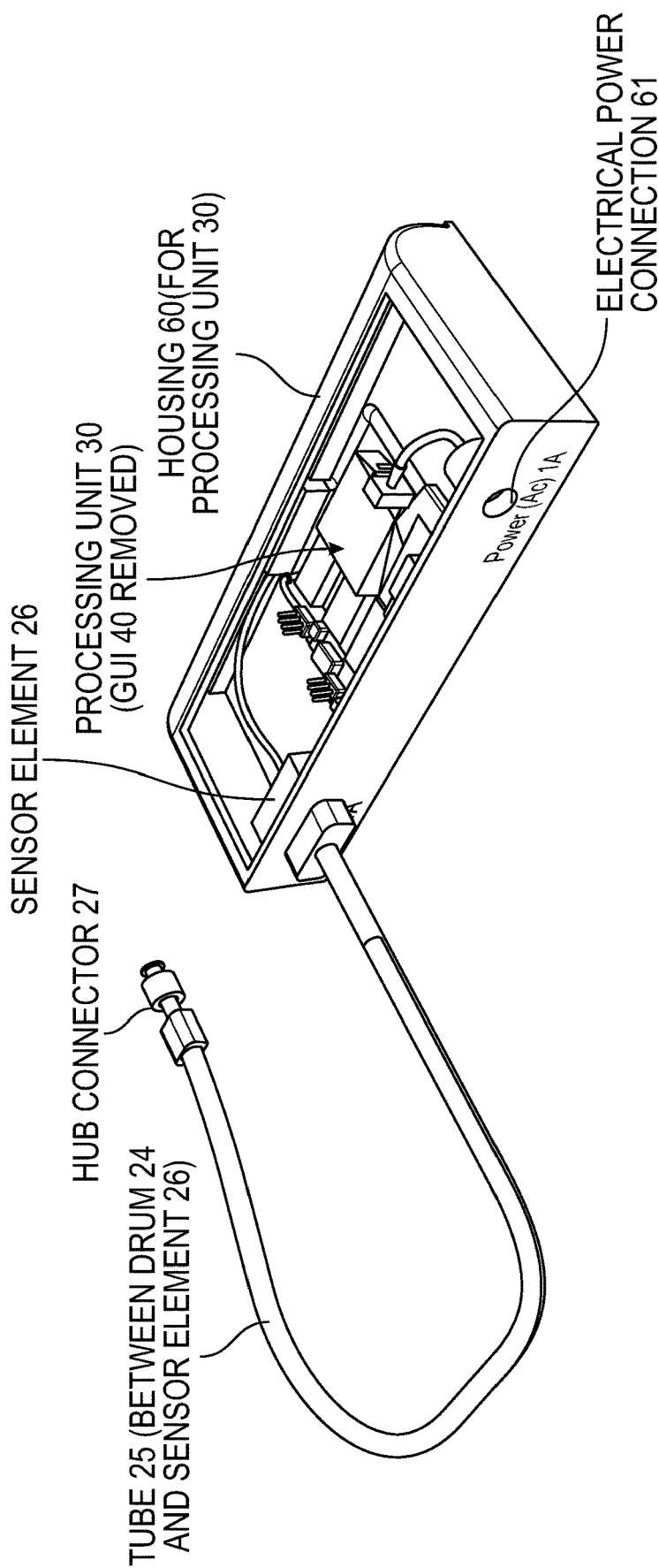
FIGURE 2B (TERMINAL VERSION)

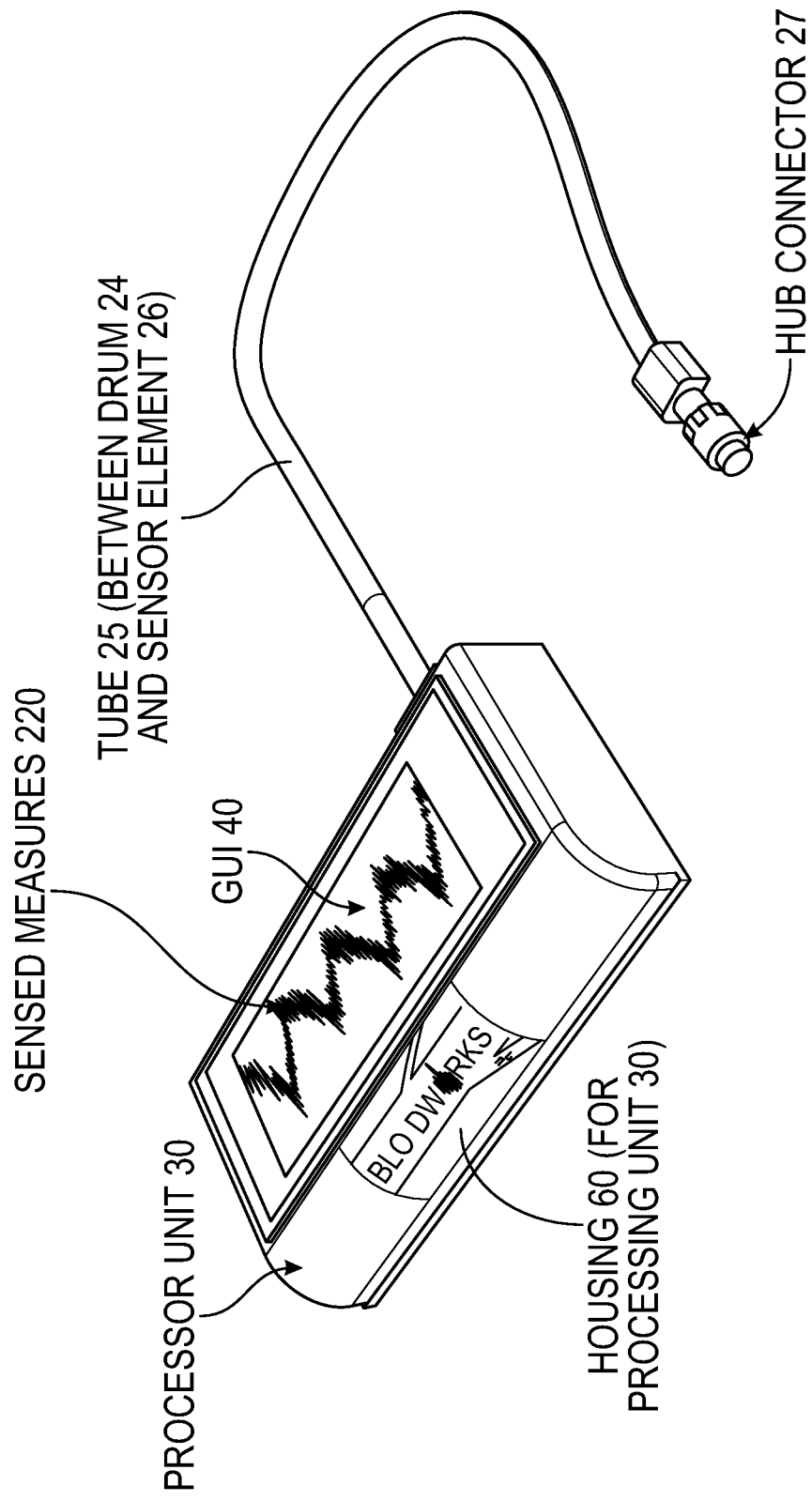
FIGURE 2C (TERMINAL VERSION)

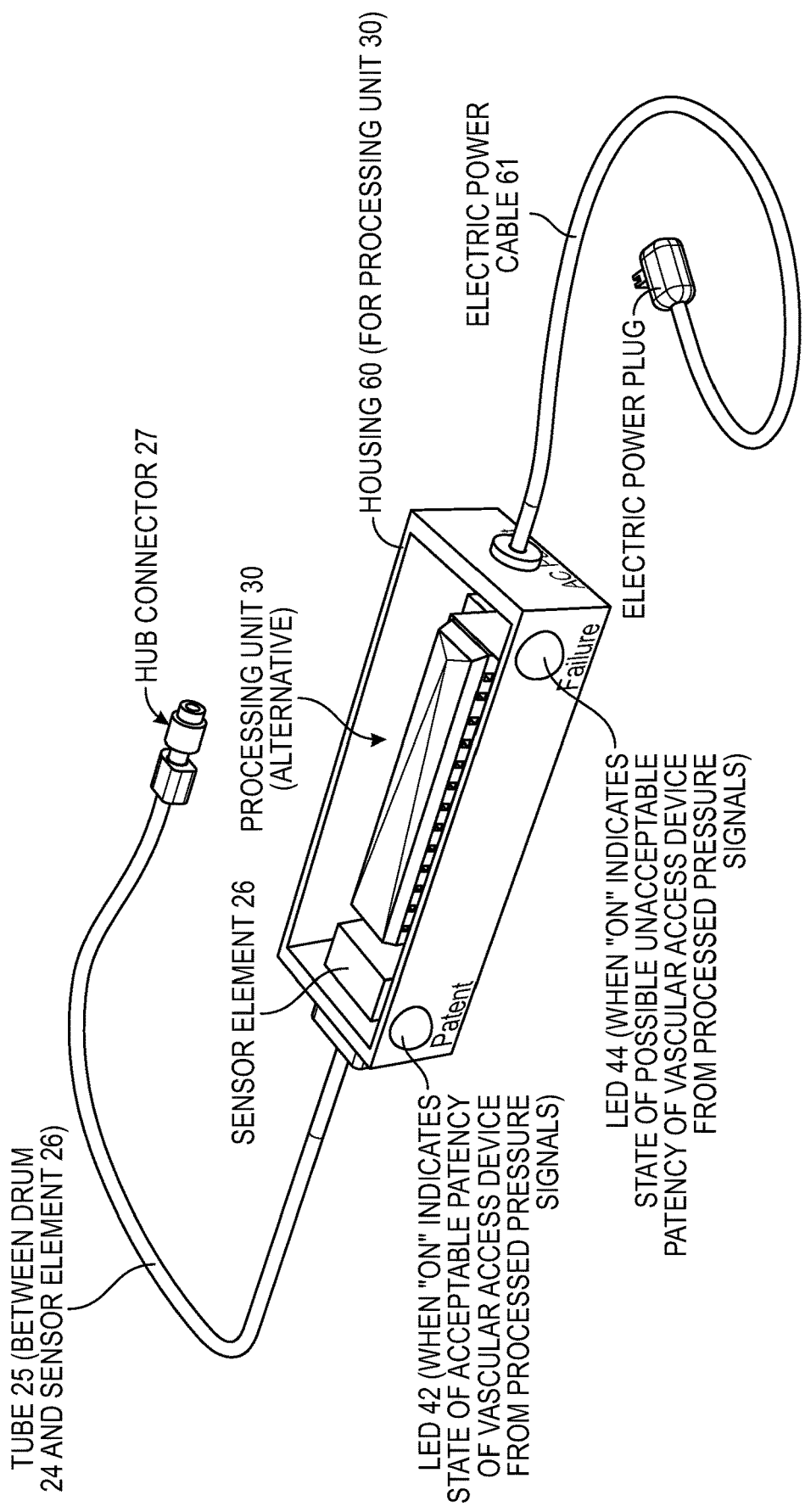
FIGURE 3 (TERMINAL VERSION)

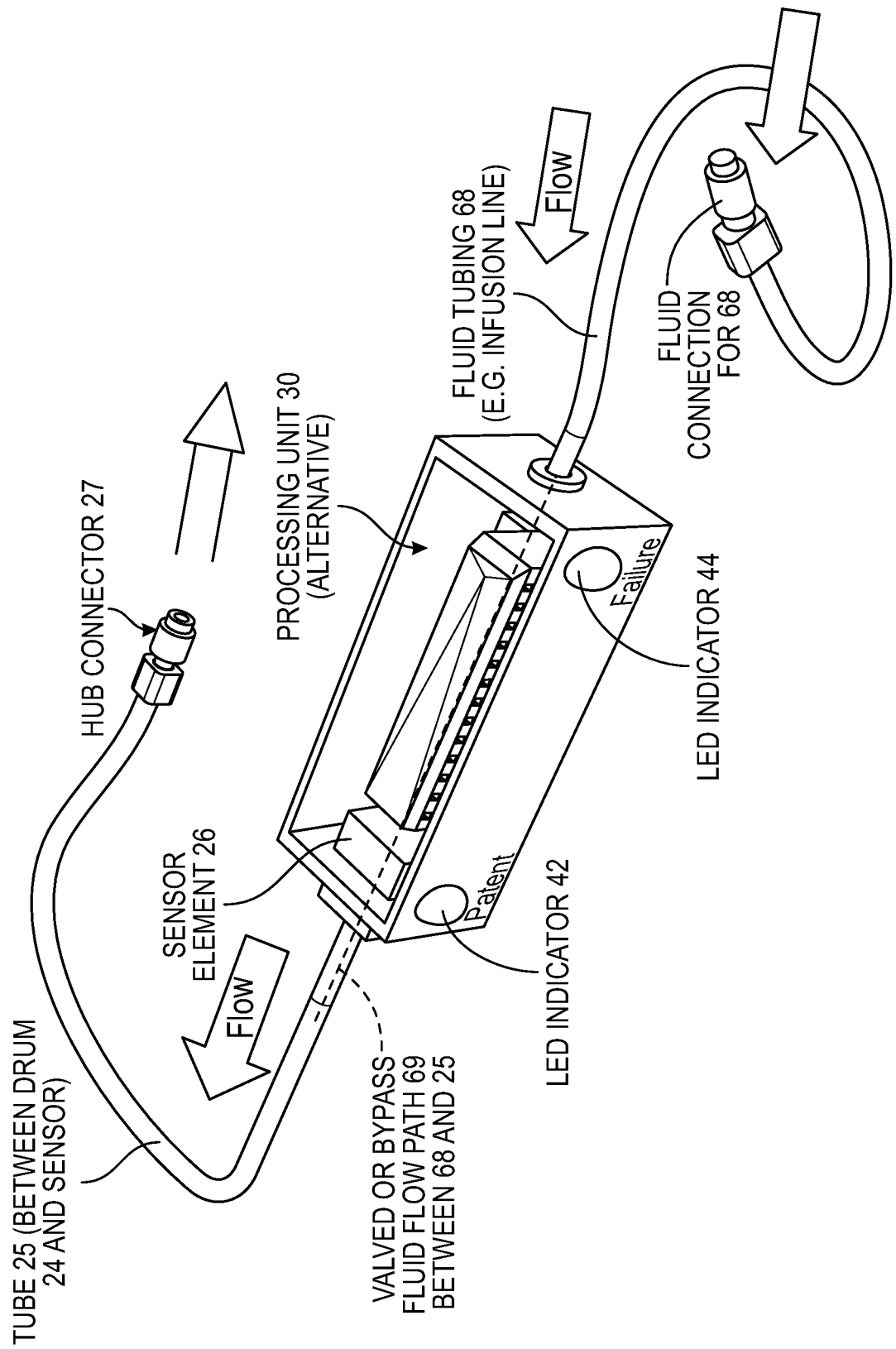
FIGURE 4 (IN-LINE VERSION)

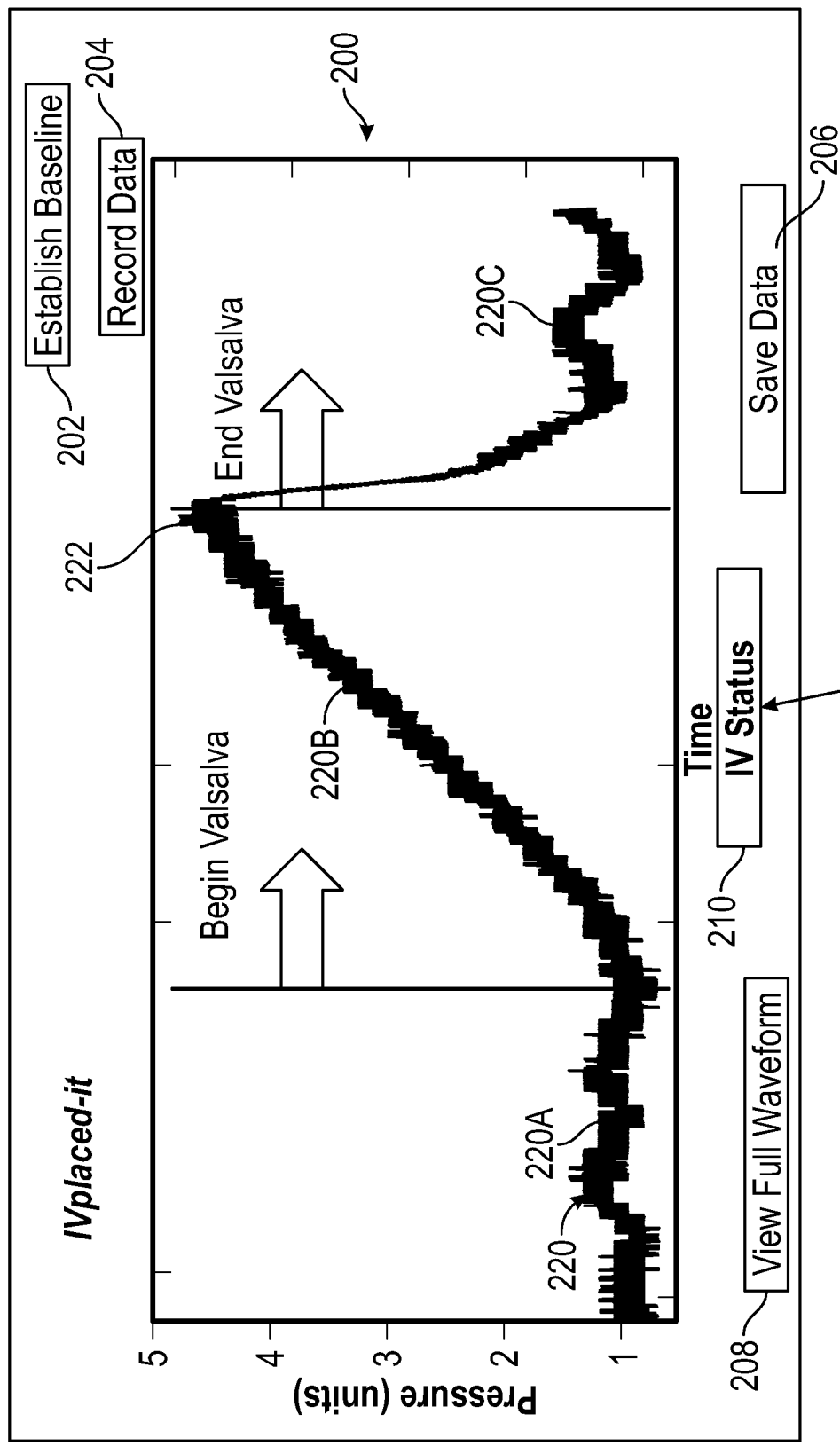
FIGURE 7 (Note : "IV Status" bar appears green to signify a positive result)

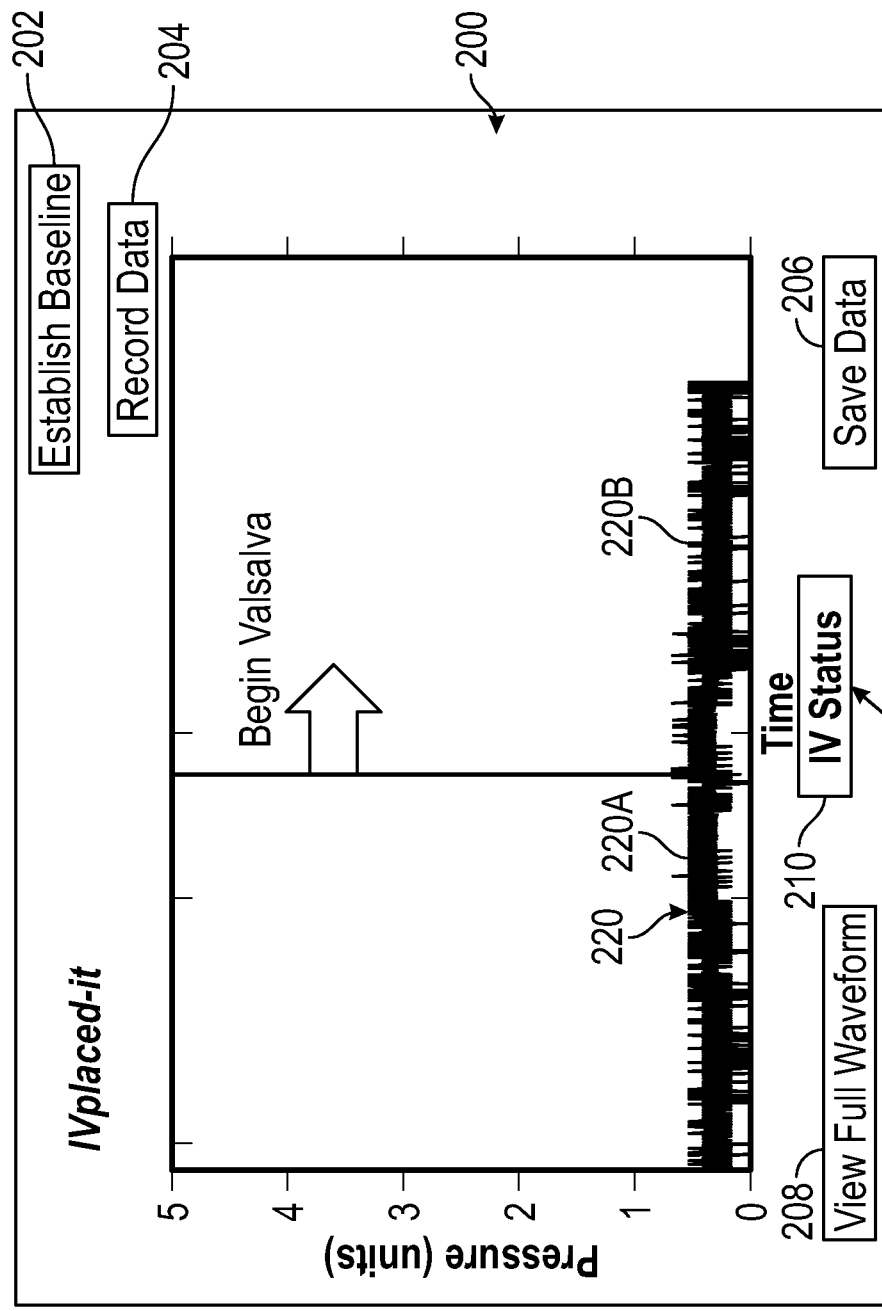
FIGURE 8 Note : "IV Status" bar appears red to signify a negative result.

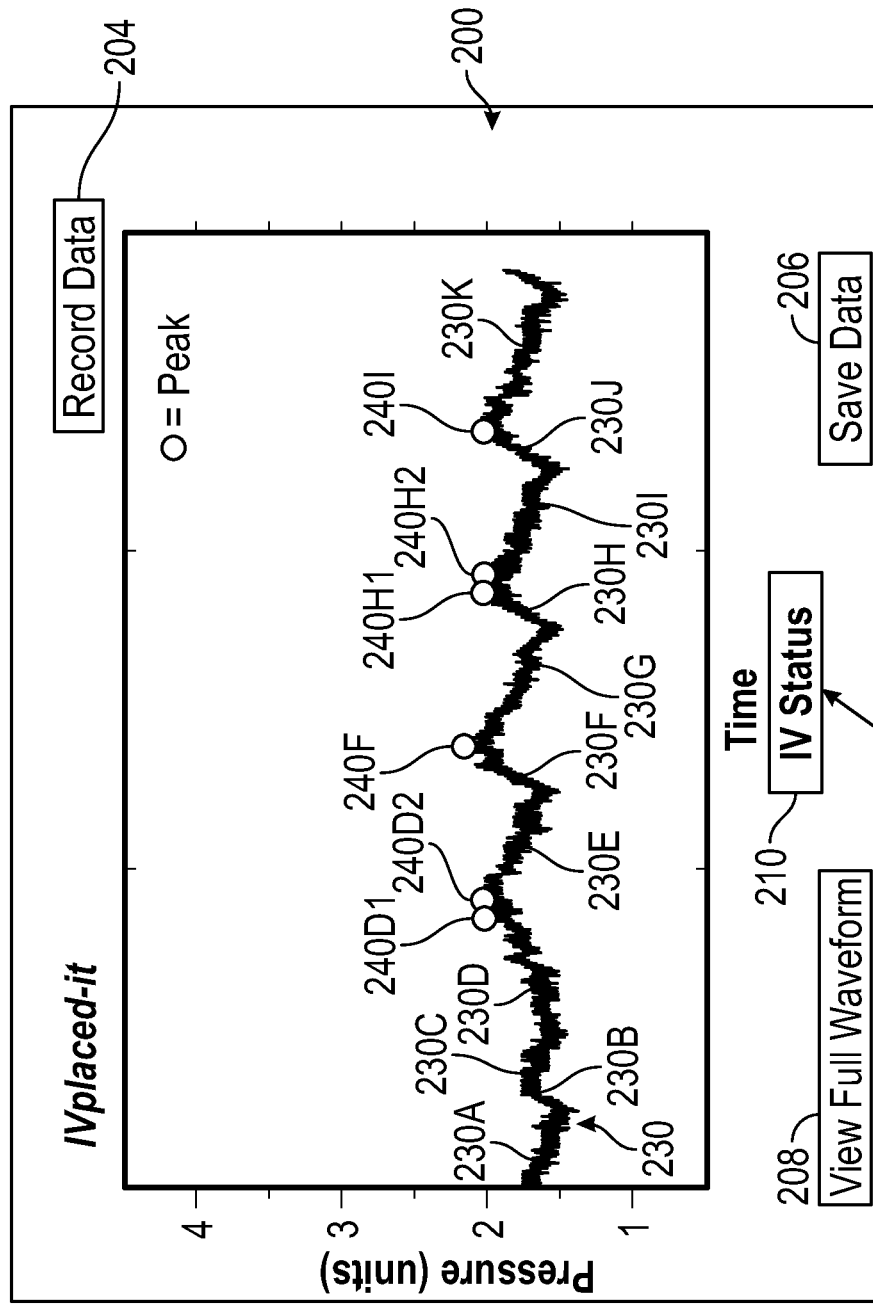
FIGURE 9 (Note : "IV Status" bar appears green to signify a positive result.)

METHOD AND DEVICE FOR VERIFICATION OF INTRA-LUMINAL PLACEMENT AND PATENCY FOR VASCULAR ACCESS DEVICES

CROSS-REFERENCE TO RELATED APPLICATIONS

This application claims the benefit of Provisional Application U.S. Ser. No. 62/584,496 filed on Nov. 10, 2017, all of which is herein incorporated by reference in its entirety.

BACKGROUND OF THE INVENTION

A. Field of the Invention

The present invention relates to vascular access devices and, in particular, to a way to automatically sense and inform a user about patency and placement of the device relative a patient.

B. Related Technology

Vascular access devices are used throughout all healthcare settings as a means by which to infuse medications and fluids into blood vessels, to remove blood from blood vessels and to monitor different physiologic parameters (i.e. arterial vascular access devices used to invasively monitor blood pressure). Insertion of such devices is difficult especially given tortuous vascular anatomy, previous use of toxic intravenous medications, and older age. Additionally, after prolonged periods between uses of the vascular access device, the patency of the vascular access device may be in question. It is essential that the healthcare worker using the vascular access device is able to undoubtedly determine that the vascular access device is located within the lumen of the blood vessel and that the vascular access device is patent. If these conditions are not properly assessed or met, there is an increased risk of drug, blood, and fluid extravasation into the subcutaneous tissues that can cause significant tissue injury and potentially lead to necrosis. Alternatively, replacement of an occluded vascular access device can lead to increased pain and delay of care.

Current methods of assessing intra-luminal placement and patency of the vascular access device are based on subjective clinical assessment. Examples of such methods include: the presence of blood return from the vascular access device, lack of localized swelling upon infusion, lack of patient-reported pain and discomfort with infusion, and subjective resistance to flushing the vascular access device by the healthcare workers. These subjective methods are not always accurate given different patient populations, scenarios, and healthcare workers. Currently, there are no methods developed to objectively conclude that a vascular access device is both placed intra-luminally and is patent.

Unreliable assessments of intra-luminal placement and patency of the vascular access device can lead to negative consequences for the patient and healthcare worker. In terms of the patient effect, localized extravasation of infused medication, fluid, or blood can lead to local tissue damage and necrosis which may require further medical intervention including potential amputation. Additionally, if the healthcare worker is not convinced of the viability of the vascular access device, the decision to place another vascular access device may be considered, which exposes the patient to additional venipuncture, pain, delay of care, and infection risk. This replacement of the vascular access device may not be necessary but can be deemed necessary based on the limited subjective assessments employed by the healthcare worker. In terms of the healthcare worker effect, the necessity to re-assess vascular access devices and consult with other healthcare workers can further delay care for the particular patient of concern as well as the other patients under the healthcare worker's care. Additionally, replacement of vascular access devices increases time spent with one patient and leads to increased staff resource utilization, especially if more than one staff member is needed to attempt placement of a new vascular access device on a difficult-to-cannulate patient.

Objective metrics are used throughout the healthcare continuum to guide medical interventions. However, in the case of assessing the viability of the most basic method by which to provide medications to an acutely ill patient, healthcare workers rely solely upon subjective and questionable methods, which do not sufficiently mitigate risk and may be deemed inadequate.

C. Physiology and Discoveries

Intra-thoracic pressure is known to change in near sinusoidal fashion as a result of respiration. During non-ventilated and ventilated positive pressure respiration, the intra-thoracic pressure changes between the inspiratory and expiratory phases of respiration. Changes in intra-thoracic pressure in both ventilated and non-ventilated individuals augment both cardiac afterload and venous return (cardiac pre-load), which are determinants of cardiac stroke volume and pumping efficiency. The changes in venous return are now known to be detectable as changes in vascular pressure. Individuals also have the ability to actively and dramatically augment intra-thoracic pressure by engaging in a Valsalva maneuver (forcefully expiring against a closed glottis). See, e.g., Proth, et al., The Valsalva maneuver: Mechanisms and clinical implications. Heart Lung. 1984. September; 13(5): 507-18, incorporated by reference herein.

Through exploratory testing performed by the inventors, it was discovered that these changes in venous return are detectable in an intra-luminally placed, patent vascular access device with quantifiable magnitude and frequency. In contrast, a vascular access device that is not patent—either due to occlusion, misplacement, or gradual loss of prior intra-luminal placement—is incapable of detecting intravascular pressure changes resulting from changes in intra-thoracic pressure.

The purpose of this device is to serve as an objective metric by which to assess intra-luminal placement and patency of vascular access devices as well as continually ensure validity of the physiological metrics recorded from said vascular access devices.

SUMMARY OF THE INVENTION

A. Objects, Features, and Advantages of the Invention

It is a primary object, feature, and advantage of the invention to provide methods, apparatus, and systems which improve over or solve problems and deficiencies in the state of the art.

Another object, feature, or advantage of the invention is methods, apparatus and systems with provide an objective metric by which to assess intra-luminal placement and patency of vascular access devices as well as continually ensure validity of the physiological metrics record from said vascular access devices.

Other objects, features, or advantages of the invention are methods, apparatus, and systems as above-described which:
a. can be accomplished automatically or semi-automatically;
b. are no more invasive than intravascular access attempts;
c. is adaptable to different patients, different patient conditions, and different intravascular access techniques;
d. can take advantage of or be integrated with at least some of standard vascular access device or system components;
e. is relatively inexpensive in both components and operation;
f. can be calibrated to sufficient accuracy and repeatability for its intended purpose and does not absolute measurement accuracy;
g. can be implemented in a variety of form factors and configurations;
h. can be continuous or intermittent in terms of measurement duration;
i. may be used to measure variations in intra-vascular pressure to aid in systemic cardiovascular condition diagnosis and management;
j. can be applied to humans or animals.

These and other objects, features, aspects, and advantages will become more apparent with reference to the accompanying specification and claims.

B. Aspects of the Invention

An aspect of the invention includes devices and methods to non-invasively determine intra-luminal placement and patency of a vascular access device. Our device is a non-invasive measure, even if the IV access itself is invasive (our device, of course, is designed to be used in conjunction with an inherently invasive device: e.g. a catheter). In one form, our device itself remains non-invasive, connecting at the vascular access device's hub outside the patient's body. The term "vascular access device" is used to describe any catheter or structure used, e.g., to gain access to the vascular system in order to administer fluids or medications, remove blood, or monitor additional physiologic parameters. The invention estimates patency and/or placement indirectly. Upon a first insertion of the vascular access device into a patient, a physiological parameter which is indicative of proper patency and/or placement of the vascular access device is measured. The measurement is compared to a reference value or calibration. If the comparison indicates indication of proper patency and/or placement, a signal is generated. The signal can be used in a number of ways. One example is to give a user-perceivable alarm or indication of proper patency and/or placement. Non-limiting examples include activating a light, an audible buzzer, a vibration, readable displayed text or graphics, or some combination of the same. The user can then have an indirect and at least semi-automatic way of estimating proper patency and/or placement of a vascular access device.

In one aspect of the invention, the technique is able to achieve this end by monitoring and detecting changes in the physiological parameter of systemic vascular pressure via pressure measurement in, at, or near the hub or other portion of a vascular access device that has a lumen placed intraluminally, and then using the results of that monitoring to indirectly transduce conditions or states indicative of either good placement/patency or bad placement/patency of the vascular access device. The monitored pressure variations would be transduced and processed relative to a priori information (e.g. references, thresholds, or other calibrations) to differentiate between good and bad states. The system can provide a sensory indication to observers (e.g. indicator light(s), GUI graphic with text, color, etc., sound, vibration, or other) to indicate state. Alternatively, or in addition, the monitoring and indication of placement/patency state can be recorded, digitally stored, transmitted to other devices, or used otherwise.

Other possible aspects of the invention may include portability, speed of measurement, objective nature of measurement, ease of use for the end-user, and affordability achieved through primarily disposable components to maintain sterility; reusable components that can be sterilized may be considered.

Another aspect of the invention includes apparatus and systems of at least semi-automatically estimating intraluminal placement and patency of a vascular access device. A sensor is integrated with or operatively connected to the vascular access device to sense a physiological parameter at or in the intravascular lumen of the device. The sensor is in turn operably connected to circuitry that can convert a measurement of the physiological parameter into an electrical or electronic signal that is proportional to a quantification of the parameter. The signal can be communicated to a component for evaluation. In one example, the component is a digital processor that compares the signal to a reference or calibration indicative of proper patency and/or placement of the vascular access device. The processor is programmed to identify from the comparison an estimate of whether or not proper patency and/or placement exists, and generate a signal. The signal can be used, inter alia, to further generate user-perceivable indications of the comparison. In one example, if the comparison indicates proper patency and/or placement, some type of human sensory indication is generated. Non-limiting examples are visible, audible, tactile, or combinations.

In one specific embodiment of the invention, the sensor senses fluid pressure in the lumen of the vascular access device after initial placement of the vascular access device in a patient. The monitored pressure is compared to reference values or calibrations of changes in systemic vascular pressure that are indicative of what would be sensed with proper patency and/or placement of the vascular access device. The system provides user-perceivable indicator if the comparison indicates proper patency and/or placement. This allows the user to have an automatic check on placement and patency. Optionally, the system can give a user-perceivable indication if the comparison indicated improper patency and/or placement. This would the user to take remedial action.

Another aspect of the invention includes a system that includes an apparatus as discussed above and practiced with the method discussed above, in combination with other components to form an overall system. The system can include an integration of the device with an external housing. The external housing can include components related to receiving sensor information, comparing it to prestored reference or calibration values, and producing the signal based on the comparison. In one example, the system includes a GUI that can at least display to the user the results of the comparison. In another example, the GUI can allow touch screen input regarding functions of the system. Examples would be on/off, begin sensing and measurement, display of vascular pressure measurements, reset, store measurements or comparisons, or communicate to other devices or systems.

Another aspect of the invention comprises a kit including pre-selected components of the above system packaged for use by a health care professional.

BRIEF DESCRIPTION OF THE FIGURES

FIG. 2B is a computer designed model of one exemplary embodiment of technology according to the invention depicting a processing unit with attached cable extending to the sensor such as in FIG. 2A via luer-lock connection to the vascular access catheter. A graphical user interface display (GUI) (not shown) can appear atop device (see, e.g., FIGS. 2C and 7-9). The top is shown open, exposing the internal processing unit to view.

FIG. 2C is the model of unit of FIG. 2B but from a different viewing angle and with a GUI installed.

FIG. 3 is a computer designed model of another exemplary embodiment of the technology, an alternative embodiment depicting a processing unit with attached cable to sensor via luer-lock connection to the vascular access catheter. LED indicator lights present to indicate state of the vascular access catheter (e.g. placement and/or patency).

FIG. 4 is a computer designed model of another exemplary embodiment of the technology according to aspects of the invention, a still further alternative embodiment depicting a processing unit with attached cable to sensor via luer-lock connection to vascular access catheter. LED indicator lights present user-perceivable indication of status of placement and patency. This is referred to as the in-line embodiment, where the device is placed between vascular tubing and the vascular access catheter for continuous or intermittent monitoring. A smaller processing unit housing than what is shown here would allow for direct luer-lock, or similar, connections between the vascular tubing and the hub of the vascular catheter.

FIG. 7 is a graphical user interface (GUI) exemplar from testing with the setup of FIG. 6 showing the results of an active pressure change (Valsalva maneuver starting at "Begin Valsalva" and ending with "End Valsalva") with a known good (e.g. patent or non-occluded, or properly emplaced) vascular access device. Note that the GUI indicates or displays a positive/proper state of patency/placement (green color at "IV STATUS" bar) consistent with a pre-determined/calibrated "good state" of the vascular access device. Also, the illustration shows sensitivity of the sensor to pressure changes at the blood vessel.

FIG. 8 is a graphical user interface exemplar from testing with the setup of FIG. 6 showing the results of a known non-patent (e.g. occluded or not properly emplaced) vascular access device. The waveform to the left of the "Begin Valsalva" marker illustrates the signal observed during passive respiration. A "Valsalva" maneuver was then performed illustrating active respiration in a not patent (e.g. occluded or not properly emplaced) vascular access device. Special attention should be paid to the lack of any signal variation regardless of subject intra-thoracic pressure changes. Note that the GUI displays a negative state (red color at "IV STATUS" bar) consistent with pre-known/calibrated "error" or possible "failure" state of the vascular access device. It also shows sensitivity of the sensor to lack of pressure changes at the blood vessel.

FIG. 9 is a graphical user interface exemplar from testing with the setup of FIG. 6 showing the results of a passive subject breathing with automatic pressure peak detection. Note the GUI displays a positive state (green color at "IV STATUS" bar) consistent with pre-known/calibrated "good" state of the vascular access device indirectly transduced from monitoring pressure variations at the vascular access device. It also shows sensitivity of the sensor to pressure changes at the blood vessel during typical patient respiration. Peaks and valleys are clearly differentiated.

DESCRIPTION OF EXEMPLARY EMBODIMENTS ACCORDING TO THE INVENTION

A. Overview

For a better understanding of the invention, examples of just a few forms the invention can take will now be described in detail. It is to be understood that these examples are neither inclusive nor exclusive of all forms and embodiments the invention can take.

B. Definitions

The following definitions apply herein:

"Ventilated" means the use of positive pressure mechanical ventilation, typically via endotracheal tube or tracheostomy.

"Non-Ventilated" means without the use of mechanical ventilator. Respiration is based on difference between atmospheric and intra-thoracic/intra-pulmonary pressure as well as diaphragm strength.

"Active respiration" means where a patient/subject is controlling their respiration in an active/forced/enhanced maneuver (i.e. Deep breath or Valsalva maneuver).

"Passive respiration" means normal "at-rest" breathing.

"Valsalva" means a forced attempted exhalation against a closed airway (closed glottis); a straining maneuver to increase intra-thoracic pressure (i.e. Straining to have a forced bowel movement).

The terms "patient," "subject," "individual," and the like are used interchangeably herein, and refer to any human or animal amenable to the methods described herein. In certain non-limiting embodiments, the patient, subject or individual is a human.

"Intravascular Pressure" means the pressure, measured in millimeters of mercury, within the lumen of a blood vessel.

"Vascular Access Device" means any catheter, or structure, used to gain access to the vascular system in order to, e.g., administer fluids or medications, remove blood, or monitor additional physiologic parameters.

"Hub" refers to the proximal end of a vascular access device, commonly terminating in a Luer-lock connection.

C. Generalized Embodiment

1. Apparatus

Figure 1A:
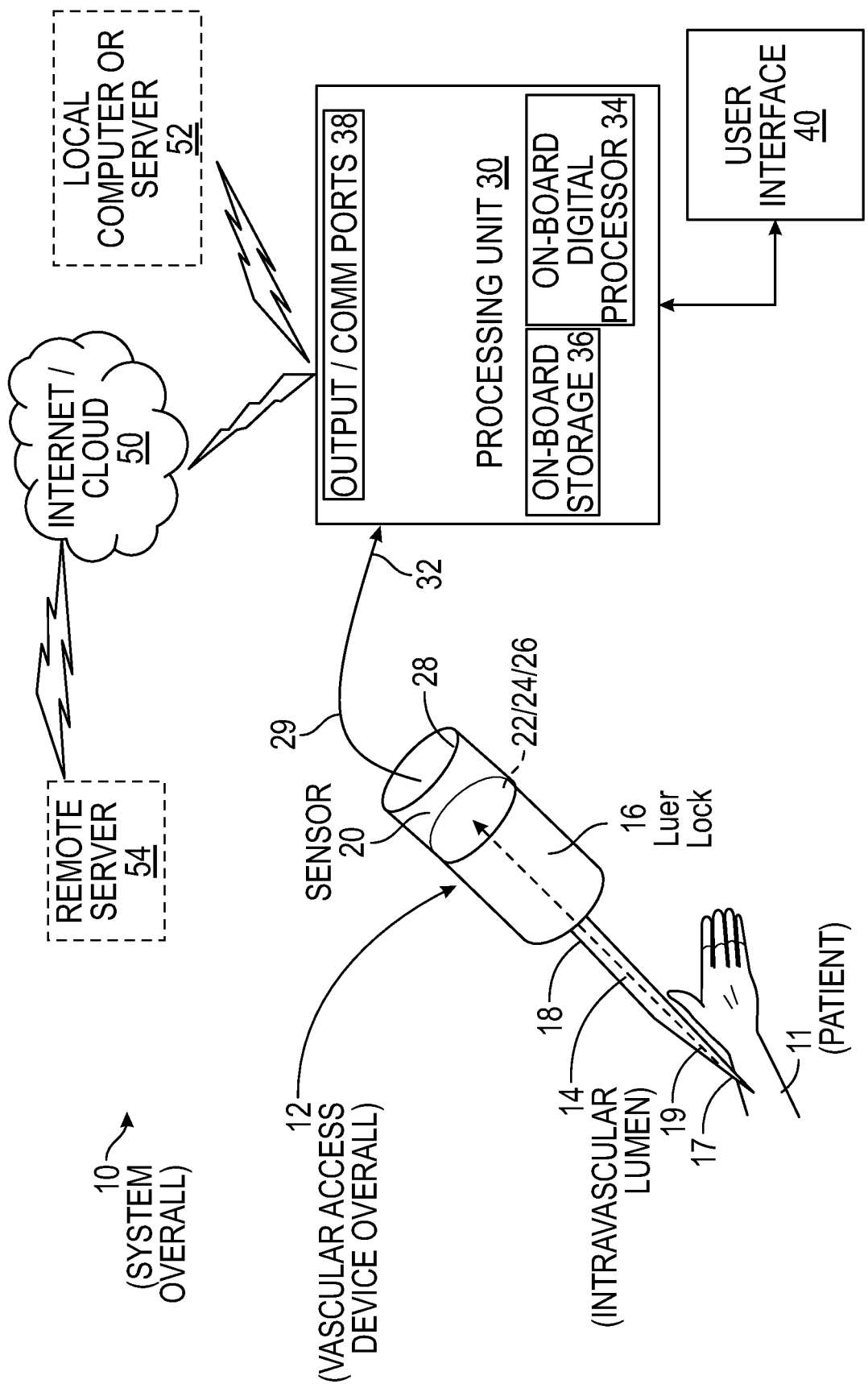
FIG. 1A is a highly diagrammatic illustration of a generalized exemplary embodiment of a system according to the invention.

With particular reference to FIGS. 1A and B, a first embodiment according to at least some aspects of the invention will be described.

A vascular access device 12 according to aspects of the invention includes not only a conventional or typical intravascular lumen (e.g. catheter) for insertion into a patient 11, but a housing that would be external of patient 11, here sometimes called a hub 16. Hub 16 can include, for example, a luer-lock connection which both supports and hold lumen 14 but also allows operative connection of other devices or connectors. Several examples are wires, tubes, with or without other connectors, values, or other functional sub-components. These are well-known to those skilled in this technical art.

Vascular access device 12, in this embodiment, also includes sensor 20. Sensor 20 here is integrated with or mounted on luer lock 16. Alternatively sensor could be separated but operable connected in a manner that the relevant sensed parameter can made at, in, or from lumen 14. As will be appreciated, the form factor of sensor 20 can vary. In one example, the form factor can be on the same generally size/scale as luer lock 16, or smaller, so that it does not add significantly to overall size or weight of the whole device 12.

In one form, sensor 20 includes a sensor element adapted to detect and measure a parameter that is indicative of proper patency and/or placement of lumen 14. By operative access to lumen 14 or what is at, in, or from lumen 14, in one form sensor 20 can sense the parameter and report the sensing to a processing unit 30.

In this example, processing unit is operably connected to sensor 20 and includes components and configuration to receive, evaluate, and generate an output based on the evaluation. In one example, processing unit can be connected by electrical connection (wired or wireless) 29 from an output port 28 of sensor 20 to an input port on processing unit 30. The operative communication or access of sensor 20 to lumen 14 is shown diagrammatically by dashed line 19 in FIG. 1A. In one example, this communication or access can be fluid pathway between in interior of lumen 14 and a sensing element 24 in sensor 20. This could be via a sensor input port 22. In one example, the physiological parameter in that case could be pressure in that pathway 19.

A sensor circuit 26 in sensor 20 can transduce a pressure measurement or plural such measurements into an electrical or electronic signal. That signal can be communicated via conductor 29 to an on-board digital processor 34 of unit 30. By pre-programming, processor 34 can compare the transduced measurement(s) to previously obtained reference(s)/ calibration(s) of what pressure should be in, at, or from lumen 14 if properly emplaced in patient 11.

A user interface 40 operatively connected to unit 30 can take on a variety of different forms. One example would simply be some sort of user-perceivable indication. Non-limiting examples include lights, sounds, tactile manifestations (e.g. vibration). If the transduced measurement(s) correlate to an indication of proper patency/placement, unit 30 can instruct user interface 40 to present the indication. The user is then informed automatically of an indication of proper patency and/or placement. This is from a quantification of an indirect measure, namely a pressure measurement in, at, or from lumen 14.

If the transduced measurement(s) do not correlate to an indication of proper patency and/or placement, unit 30 can, in one example, not generate a user-perceivable indication of the same. The user is then informed that a positive indicate of proper emplacement has not been derived by unit 30 and the user can take remedial steps. On the other hand, in some embodiments, unit 30 can issue a user-perceivable indication of estimation that patency and/or placement is not proper or effective based on the comparison. This would give the user an affirmative indication of such status. The user-perceivable indication in most cases would be clearly and easily distinguishable by the user from an indication of proper emplacement. For example only, one color indicator light could be used for proper emplacement and a different color for improper.

As will be further appreciated, user interface 40 could take other forms, or could be a combination of different user-perceivable indicators. It could also have other functions. For example, either in addition to indicator lights of proper or improper estimation of emplacement, interface 40 could present audible, tactile, or other user-perceivable indications. Non-limiting examples could be a display with textual or graphic indications, a vibratory device, or a speaker.

Still further, interface 40 could have a display (e.g. LCD or other) that could display other information to a user than an indication of state of emplacement of lumen 14. Non-limiting examples could be textual or graphic information about the parameter, the measurement(s), about the user, about the patient, etc. In one example, user interface 40 could be a digital display. In another example, user interface 40 could be both a digital display but also a touch screen. The touch screen could present prompts, menus, instructions, virtual buttons, or other graphic user interface (GUI) functionalities for operation of the overall device and how the results are processed or used.

It will be appreciated that sensor 20 would be capable of detecting and differentiating some characteristic of the parameter being measured. In the example of pressure, such could include magnitude of sensed fluid (liquid or gaseous state or both) at any point in time. It also could include magnitude at different discrete points of time or continuously over some time period. Sensor 20 would have the ability to convert, transduce, or otherwise convert measurement(s) of the sensed parameter into a signal that can then be communicated, transformed, translated, or otherwise used by processing unit 30.

As diagrammatically indicated in FIG. 1A, further functionality of unit 30 is possible. Some non-limiting examples are on-board storage of digital information. This could include, by example only, pre-programming, storage of calibration models or data, and storage of measurements or comparisons.

2. System

Additionally, FIG. 1A diagrammatically indicates optional possible functionalities of communication of unit 30 with other components or sites. Such an overall system 10 could include one or more of the devices 10 discussed above in communication with other devices.

Non-limiting examples are one or more other local devices 52 (e.g. a local computer or network (e.g. LAN)), or one or more remote devices 54 (e.g. computers, servers, or networks (e.g. WAN) via Internet or cloud 50. Such communications, devices, and systems are well-known to those in the technically art, as well as the apparatus and techniques to connect and use them.

3. Operation

Figure 1B:
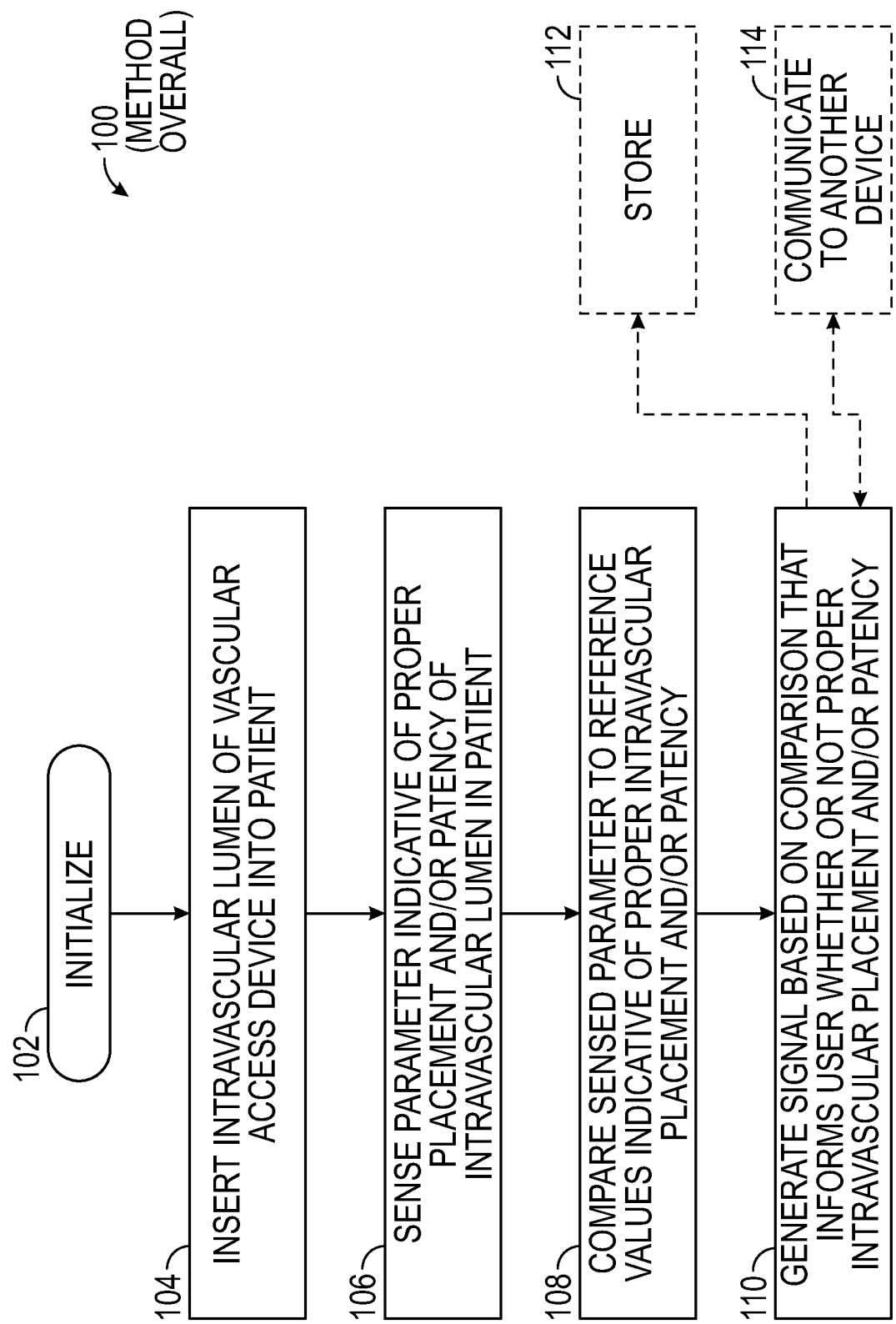
FIG. 1B is a flow chart of one possible exemplary method according to the invention.

With reference to FIG. 1B, a flow chart of an example of one method of use 100 of the apparatus/system discussed above is set forth.

Initialization (Step 102). In most cases, the physiological parameter to be measured would have some characteristic that is indicative indirectly with proper lumen 14 patency and/or placement in the blood vessel of a patient. One example is pressure measured in, at, or from the contents of lumen 14. Method 100 would first obtain or create reference or calibration information about what sensed pressure of a properly emplaced lumen 14 should be with the given arrangement of, e.g., the selected sensor 20.

Insertion of lumen 14 into patient 11 (step 104). The user than inserts the distal end of lumen 14 into the patient.

Measurement after emplacement of lumen 14 (step 106). A measurement or measurements are then acquired.

Comparison to reference or calibration (step 108). The acquired measurement(s) is/are then compared to the initialized reference or calibration. The comparison yields an estimation of whether or not there is a positive correlation or negative correlation to measurement values indicative of proper patency and/or placement.

Signal Generation of the Correlation (step 110). The estimation is used to generate an electrical or electronic signal. In one example, the signal activates some user-perceivable indication of positive correlation to inform the user of the same. In another example, the signal activates some user-perceivable indication of either positive or negative correlation, so that the user gets feedback either way. In another example, the signal activates any of the foregoing, plus other user-perceivable information. Non-limiting examples include such text or graphic display of measurements relative to reference or calibration models.

As indicated in FIG. 1B, other options include storage (step 112) of measurement or correlations, and/or communication of measurements or correlations or other information with one or more other devices.

As can be appreciated from the foregoing, the generalize embodiment meets one or more of the aspects, objects, features, or advantages of the present invention. For example, the apparatus/system of FIG. 1A and method of FIG. 1B each provide a user at least semi-automatic estimation of proper vascular access device placement based on measurement(s) of a parameter indirectly correlated automatically with an indication of proper patency and/or placement.

D. Specific Example/Embodiment

With additional reference to FIGS. 2A-C, and 3-9, a specific example/embodiment of one form the invention can take will be set forth. This embodiment will follow the basics of the generalized embodiment discussed above. Aspects of the generalized embodiment apply here.

1. Apparatus a. Vascular Access Device and Sensor

In this embodiment, vascular access device 12 has a typical lumen 14 and hub 16. It is modified to add sensor assembly 20.

Figure 2A:
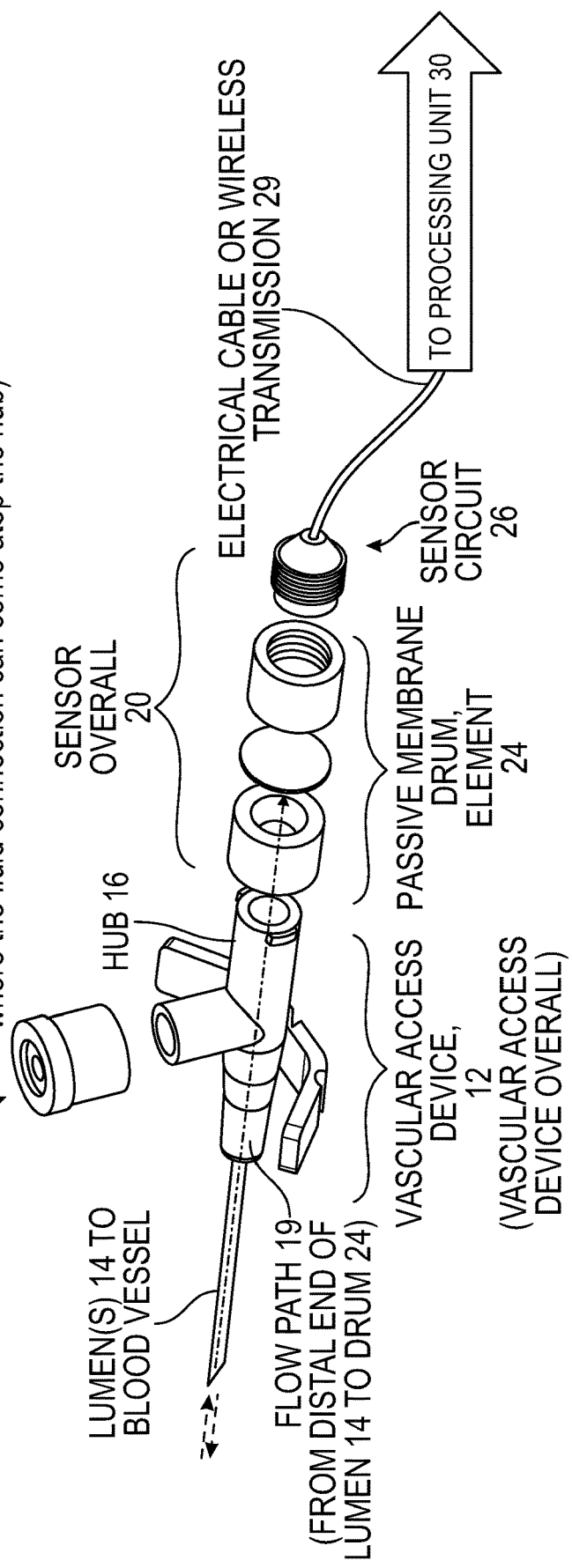
FIG. 2A is a computer designed model of one exemplary embodiment of technology according to the invention, in particular depicting in exploded view a vascular access device and physiological parameter monitor in the form of a vascular access catheter operably connectable to a passive drum membrane that is, in turn, in operative communication with a pressure sensor.

Conventional hubs 16 have internal conduits or fluid paths in communication with the internal lumen flow path of lumen 14. In this embodiment, a tube 25 is created that mounts in sealing fashion to an opening at the proximal end of hub 16. Tube 25 can be of a variety of materials and form factors. Essentially it provides good fluid communication with hub 16 and, in turn, lumen 14. A variety of medical-grade plastics, metals, or other materials are possible. Connection to hub 16 can be conventional (most hubs have the same built-in such as threading or interference fit). A sensor element or circuit 26 is mountable to the opposite end of tube 25. It can be sealingly as with complementary male-female threading or otherwise. Essentially it provides good fluid communication with the interior of tube 25 and in at least a substantially sealing manner. This embodiment allows removal of sensor 26 such as for maintenance, use in another device, or replacement. As shown in FIG. 2A above hub 16, the input/output from blood vessel can also come off a Y-connector behind the "sensor overall", distal to that component. See Y-connector in FIG. 6 where sensor and fluid tube come off back end of catheter hub. This graphic of an IV catheter shows one version where the fluid connection can come atop the hub.

The above-combination provides fluid communication between the distal end of lumen 14 and sensor element 26.

Sensor element 26 is a small, relatively inexpensive pressure sensor. A variety of these sensors are availability commercially off-the-shelf. They transduce fluid pressure experienced at its sensing element. In this embodiment, sensor 26 transduces physical fluid pressure into an electrical signal with is proportional to magnitude of pressure. Sensor 26 transduces pressure continuously over time. The technique to transduce pressure will be discussed in more detail later.

As can be appreciated from the exploded view of FIG. 2A, to prepare device 12 for use, lumen 14 is operably mounted to the distal side of hub 16, tube 25 is operably mounted to the proximal side of hub 16, and sensor 26 is operably mounted to the proximal end of tube 25. Sensor 26 has an electrical cable or wire that is configured for connection to a processing unit, as will be discussed below. This allows the transduced electrical signal proportional to sensed pressure at sensor element 26 to be sent for analysis.

As will be discussed further later, FIG. 2A shows the option of a passive membrane drum element 24 to be mounted intermediate the ends of tube 25. Its features will be discussed later in more detail. One function of it would be to add the ability to block passage of biological fluids of the patient to sensor element 26. Element 26 would still sense pressure changes in tube 25 because although membrane 24 would be permeable to air/gases, the fixed volume of space between it and pressure sensor 26 would transduce movement of membrane 24 in response to fluid against its distal side to pressure changes at sensor 26 via the fixed volume of air. It is to be understood membrane 24 is optional.

Another option is placement of sensor element 26. In FIG. 2A it is mounted/integrated at hub 16. An electrical wire 29 is all that is needed to communicate transduced pressure measurements of 26 to a separate processing unit.

FIG. 2B shows a different configuration. The sensor element 26 is mounted in the separate processing unit 30. Tube 25 is an elongated flexible tube having a threadable connector 27 at its distal end that can be directly operably connected in fluid communication to the proximal end of hub 16. Because tube 25 would be sealingly connected to hub 16, it would likewise to lumen 14. This would allow measurement of pressure proportional to what is experienced at lumen 14, even though pressure sensor element 26 is farther away (e.g. inches to several feet) from lumen 14.

b. Processing Unit

With particular reference to FIG. 2B, further details about processing unit 30 will be discussed.

Processing Unit 30 is responsible for recording and interpreting the continuously measured pressure waveforms, operating the decisional algorithm, and returning information to the end user. The Processing Unit 30 can take a variety of configurations. For example, it could be a module with an on-board pressure sensor 26, connected by an elongated tube 25 to a conventional vascular access device, as shown in FIGS. 2B, 2C, 3, and 4. As mentioned above, alternatively (as in FIG. 2A), could connect by just conducive wire 29 to a pressure sensor 26 mounted to conventional vascular access device 12. Whether pressure sensor 26 is at device 12 or in unit 30, the basic functions are as follows.

Figure 5:
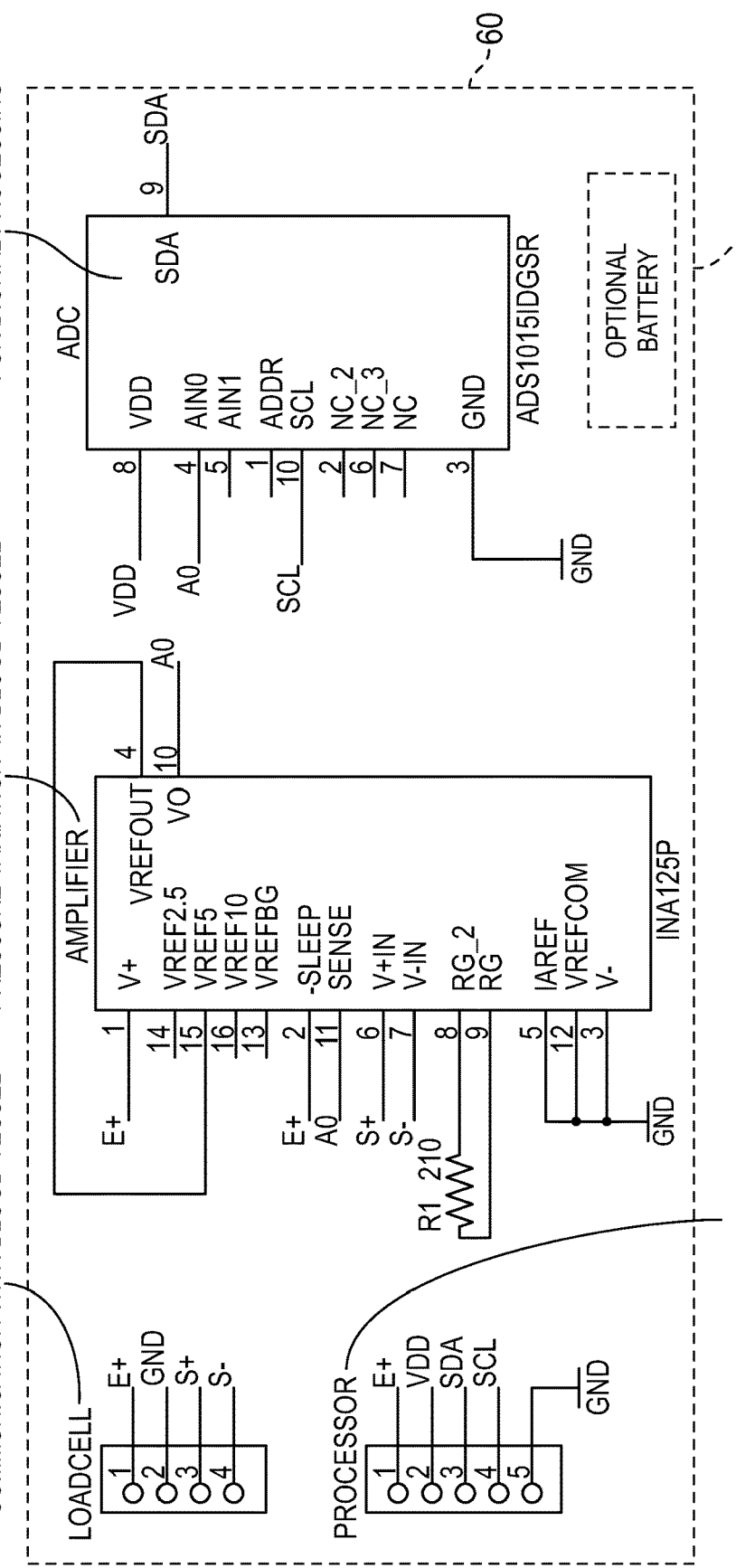
FIG. 5 is an electrical schematic of basic technology functionality and components according to one possible exemplary embodiment. Alternative components and arrangements may be utilized. Existing components may be modified, added, removed to maintain intended functionality.

A module or housing 60 (e.g. hand-sized) could include circuitry such as FIG. 5. It could further include a display (digital GUI 40, including touchscreen or other user input/output). It could be made fairly ruggedized at least acceptable for in-hospital use around fluids and other typical substances. As shown (compare FIGS. 2B/2C and 3 to FIG. 4), unit 30 could be a terminal unit (e.g. connected as a termination to the pressure sensor and not in-line with communication between the vascular access device and any source of fluids or other substances/components to send to or take from the vascular access device), or in-line in the sense that it is between (partially or wholly) the path between the vascular access device and any source of fluids or other substance/components to send to or take from the vascular access device). The in-line version (FIG. 4) would have a tubing or other conduit 68 pass through the processing unit housing 60 to allow a flow path (see diagrammatically depicted at dashed line 69) between vascular tubing 25 and the vascular access device 12 as shown in FIG. 4. Electric wires or cables could route back to the in-line processing unit (either inside or outside the fluid tubing 25 or 68 or perhaps along or integrated with the fluid tubing but isolated from any fluid passing through the tubing) to communicate electrically transduced pressure measurements at the pressure sensor back to the processing unit circuit 34. Furthermore, the processing unit 30 could be miniaturized or even micronized and might include battery power. Such components are commercially available. This could allow a much smaller form factor than suggested in FIGS. 2B-4. This might allow the whole processing unit, or a substantial part of it, to be housed right at the pressure sensor and be of at least similar form factor. Further, instead of hard-wired communication between sensor and processing unit, or processing unit and other digital device (e.g. desktop computer, tablet computer, smart phone, server (including internet), wireless transceivers could be used. Such are commercially available.

c. GUI

Graphical User Interface 40—Patient data and testing selection can occur here via user input. As mentioned, non-limiting examples of commercially available GUIs could include simply passive indicators (LED indicators (see 42 and 44 in FIGS. 3 and 4), audible buzzers, tactile vibrators, or combinations), but also passive displays (e.g. LCD), but furthermore sophisticated displays with both output and user input (e.g. touchscreen, keyboard, buttons, etc.). In the example of FIG. 3, the following states can be visually indicated with LEDs 42 and 44; LED 42 when "on" indicates state of acceptable patence of vascular access device from processed pressure signals. LED 44 when "on" indicates state of possible unacceptable patency of vascular access device from processed pressure signals. Form factor can vary according to designer need or desire and depending on the intended or desired functionalities. Following algorithm interpretation of input sensor data in the processing unit, display of data output can occur at GUI 40. As will be appreciated by those skilled in this technical area, processing unit 30 can be programmed according to the capabilities of the processor selected by the designer and to need or desire. Non-limiting examples include:

(1) Through apriori empirical testing with a selected sensor and vascular access device set-up, develop reference models of sensor output signals deemed indicative of good state of emplacement/patency of the vascular access device and indicative of bad state of emplacement/patency. Those references could then be stored, programmed into, or otherwise accessible by the processor when the system is used on an actual patient.

(2) Digitization of the sensed pressure at the vascular access device makes such comparison of pressures from an actual patient with references straightforward. Importantly, such comparison does not necessarily require perfect correspondence between actual measurements and references. In other words, the system could be programmed to differentiate between good and bad states by estimating whether actual measurements are closer to a reference indicative of a good state or a bad state. Non-limiting examples could include setting thresholds that indicate the same, or using some pre-set margin-of-error, or using some type of curve-fitting approximations.

(3) Importantly, an aspect of the invention is that determinative of the state (placement/patency good or bad) of the vascular access device is based on indirect techniques. And those techniques are at several levels. For instance, the pressure variations relate to pressure variations caused by blood or fluid movement in the vascular access device. The invention makes the insight that such blood or fluid movement would typically produce a recognizable time-based pattern or waveform related to patient respiration. As such, the invention combines these characteristics to look for patterns of sensed pressure variations indicative of either the state where the vascular access device can be reasonably assumed to be in a first state, namely it is assumed to be properly placed and/or have patency for its intended purpose; or a second state, namely it is assumed to be improperly placed and/or lack sufficient patency for its intended purpose. To differentiate between the two states can be an approximation or otherwise does not have to be (but could be) based on absolute pressure values. These subtle features and insights allow the invention to take advantage, indirectly, of measurable parameters, which can be used to estimate state of placement/patency.

d. Sensor

Sensor 26 in this embodiment is used to detect changes in the intravascular space. It may or may not be disposable. In one example, the sensor is also capable of using both higher and lower sampling frequencies in order to achieve superior temporal resolution, if desired. The type of sensor, its way of transducing pressure, and its operating characteristics can vary according to designer need or desire. Table A includes specifications of one example of a sensor (see example of a load cell sensor 26 in FIG. 5) used during testing, namely Beltran® Model 6199, 6200 or 6238 available commercially from Utah Medical Products, Inc. of Midvale, Utah, USA. Further technical details can be found at http://www.utahmedicalproducts.com/oemdpt.htm Downloaded Nov. 8, 2017 (on-line information) and Deltran® Technology for Critical Care, Utah Medical Products, Inc., Closed Needleless Arterial Blood Collection System Publication Number P/N 5831, Rev 102204 (brochure 8 pages), both of which are incorporated by reference herein. This is exemplary of the type of sensor; other embodiments and specification variations may be used.

TABLE A

Deltran ® Disposable Pressure Transducer (2017)

| | |
|---|---|
| Continuous Flow Rate (for models 6199, 6200 and 6238) | 3 cc/hr (+2/−1 cc/hr) or 30 cc/hr (±10 cc/hr) at 300 mmHg |
| Operating Pressure Range | −50 to +300 mmHg |
| Sensitivity | 5 μV/V/mmHg, ±2% (typically ≤ ±1%) |
| Zero Drift With Time | ≤±1.0 mmHg/8 hours after 10 min, warm-up to operating temperature |
| Leakage Current | <2 μA @ 115 Vac rms at 60 Hz |
| Unbalance | ±75 mmHg |
| Overpressure Protection | −400 to +4000 mmHg |
| Operating Temperature | 15° C. to 40° C. |
| Excitation Voltage and Frequency | 2 to 10 Vdc; or Vac rms to 5 kHz |
| Operating Life | >500 hours |
| Storage Temperature | −25° C. to +65° C. |
| Defibrillation Withstand | 5 discharges/5 minutes of 400 joules @ 50 ohm load |
| Natural Frequency | >200 Hz in saline |
| Phase Shift | <5° at 5 kHz |
| Output Impedance | 270 Ohms to 400 Ohms |
| Input Impedance | 270 Ohms to 400 Ohms |

The designer would take the generated output from the sensor element such as the Deltran® sensor above, and communicate its electrical analog output signal (proportional to sensed pressure at the sensor element) for processing by the processing circuit or unit. As indicated in FIG. 5 (one non-limiting example) that circuit can operate on the sensor signal such as amplify it (see amp 62) and condition it for analog to digital conversion (see component 64) into a form that can be processed by a digital processor (e.g. microprocessor 34). The processor can determine a state and output an instruction for display, recordation, storage, communication, or other use of that determination. A basic possible instruction is to simply turn on one of two LEDs 42 and 44 indicating patency or failure (see FIGS. 3 and 4). An alternative is display of state on a GUI display 40 (one example being the Green or Red color of an icon on a digital display (the "IV STATUS" icon or bar 210 in FIGS. 7-9). As indicated in those figures, there could also be graphical display of the sensed pressure (see waveforms 220). This information could be used to supplemental any indication of binary state (patency versus failure). Or it could be used to predict indications of other than optimal functioning of the vascular access device (e.g. in terms of placement or patency). But it might also be used for other purposes, including monitoring patient physiological parameters.

U.S. Pat. No. 4,658,829 to inventor Wallace and assigned to Utah Medical Products, Inc and U.S. Pat. No. 6,117,086 to inventor Shulze and assigned to Sunscope International, Inc., both incorporated by reference herein, provide background information about different types of pressure transducers and how they can be calibrated and generate a signal that can be used for quantification of pressure. These are just a few examples of both types of sensors and types of systems that can process sensor output into values correlated with pressure variations. In the example of FIG. 5, certain components can have the following functionalities: Pressure Sensor Element 26: directly or indirectly in fluid communication with blood vessel. Amp 62: amplify and condition analog loadcell signal indicative of pressure variation in blood vessel. ADC 64: convert amplified analog loadcell signals to digital signal for digital processing. Processor 34: digitally process digital ADC signal relative to predetermined references indicative of valid placement and patency or not (state) of the vascular access device; and provide output signal indicative of state (placement and patency) for display, digital storage, or other use.

e. Passive Membrane 24 (Optional)

With reference to FIG. 2A, an optional passive membrane 24 could be placed between the fluid in the vascular access device 12 and the pressure sensor 26. If a reusable sensor 26 is used, which would typically be a higher-fidelity and more expensive sensor, the disposable passive membrane unit could be selected to create a barrier between the catheter/blood and the reusable sensor. The reusable sensor 26 would normally have to be sterilized. If a disposable sensor is used, typically there is a passive membrane built into those commercially available sensors already. The passive membrane 24 may be made of medical grade silicone and can serve as a disposable component, which isolates the costly pressure transducer and computer from the subject and other substances that could harm or affect the pressure transducer and its operation. This disposable component not only limits interaction between the pressure transducer and the subject but also serves as a sterile barrier and infection control mechanism. As the function of the membrane is passive, it imposes neither a positive nor a negative pressure on the transducer but rather transmits the changes in pressure from the vascular access device's lumen.

As indicated at FIG. 2A, membrane element 24 could be encased within a hollow, cylindrical drum unit 25 with one end threaded in a Luer-lock connection. The membrane 24 must be compliant enough to be able to observe changes in pressure on the order of 0-100 mm Hg. It is substantially impermeable to fluid and gas. It would flex in proportion to the fluid in the vascular access device. This in turn would exert proportional pressure on sensor 26 because the space between sensor 26 and passive membrane 24 is fixed, which would be used for processing by the processing unit in a manner discussed above. Alternatively, an inert fluid or even semi-solid could be placed between passive membrane 24 and sensor 26 as a medium that could transfer pressure changes of the fluid in the vascular access device 12 to pressure sensor 26. Non-limiting examples of such inert fluids and semi-solids silicon oil, glycerine, halocarbon, distilled water and propanol mixture, medicinal white mineral oil.

2. System

As will be appreciated by those skilled in the art, the specific embodiment of FIGS. 2A-5 can be configures in a number of ways. Further, it can include optional functionalities, including but not limited to those discussed with regard to FIGS. 1A and B, including on-board data and programming storage, and outputs including communication with other devices either local or remote.

3. Operation

As indicated herein, the designer could allow initialization that could include pre-programming and on-board digital storage.

Initialization could include performing calibration so that actually transduced pressure measurements from sensor 26 can be effectively used to determine conditions indicative of proper patency and/or placement, or not, of the vascular access device.

Alternatively, reference values or models can be developed a priori and loaded into the processing unit to which actual pressure measurements can be compared. Still further, the reference or calibration information can be stored on-board processing unit 30, or accessible from local or remote digital storage.

Non-limiting examples of how the calibration or reference information can be created or developed, and how it can be done via the system 10 itself are set for below. Also, non-limiting examples of how measurement(s) can be displayed on a GUI and the user informed of whether or not proper patency/placement is deemed detected, are set forth. These are examples only. Variations are, of course possible. Proof of concept is also shown below.

4. Experimental Methods Summary

Figure 6:
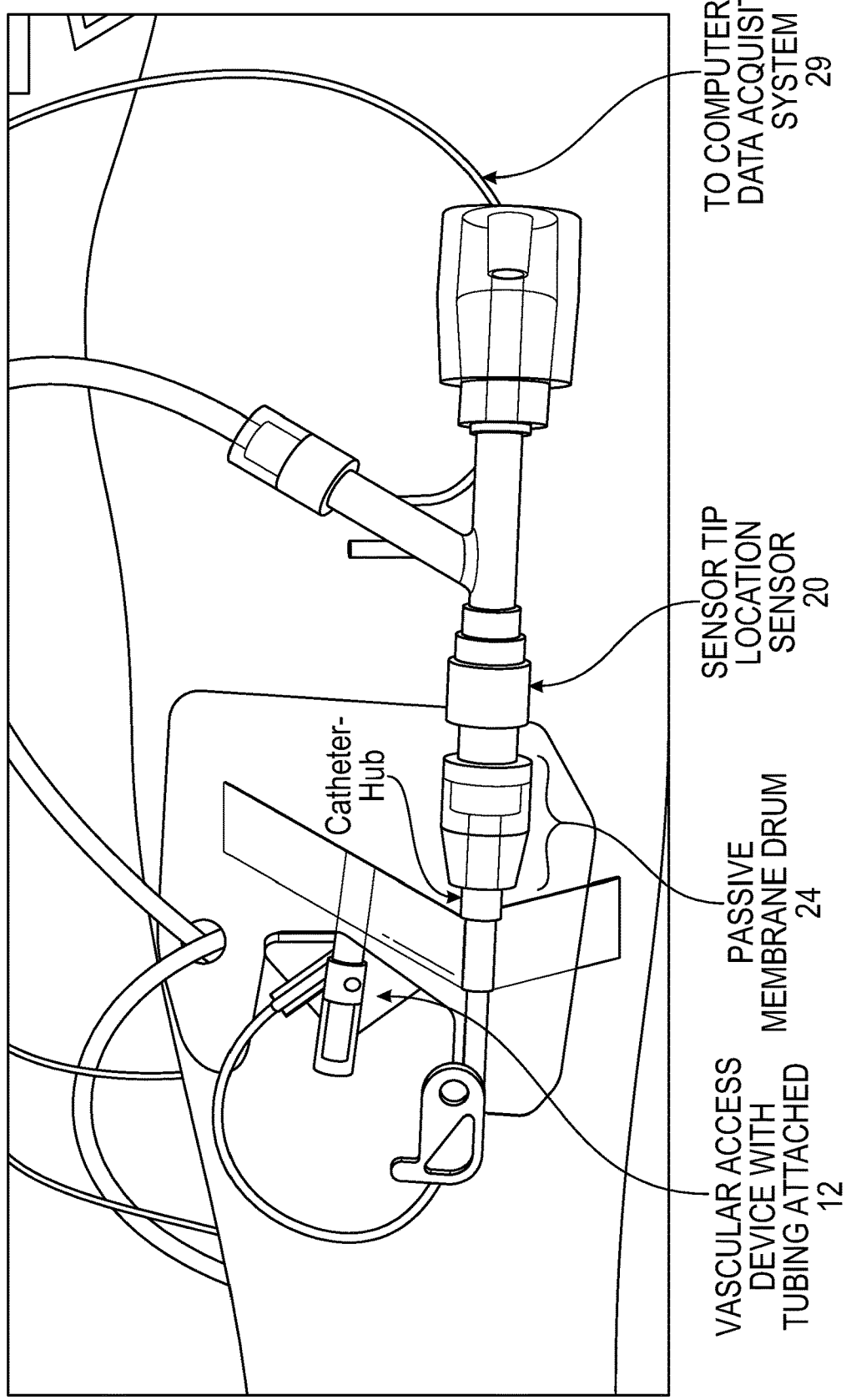
FIG. 6 is a photograph of an example a vascular access catheter device setup from testing in a human subject according to aspects of the invention.

Testing of the device of FIG. 6, which is diagrammatically depicted in FIG. 2A, began with a subject signing an informed consent form. Following this, a registered nurse placed a good (known patency) peripheral intravenous catheter in the subject's left arm and an intentionally bad (non-patent) intravenous catheter in the right arm. Compare FIGS. 7 and 8. The technology according to FIG. 6 was attached to the patent intravenous catheter, and the subject was instructed to lay supine for all stages of testing. The subject was monitored during all stages of testing by the same registered nurse. Successful outcomes were defined as positive identification of the patent intravenous catheter and negative identification of the non-patent intravenous under both active and passive intra-thoracic pressure changes. Testing figures and results are summarized in FIGS. 6-9.

Stage 1 of testing focused on active pressure changes: ideal for conscious patients. Recording was initiated using the graphical user interface 40 (see version at ref. no. 200 in FIG. 7) and the subject was first asked to breathe normally for approximately 5 seconds while a baseline was established (see waveform from continuous pressure sensor measurements at 220 in FIG. 7; and in particular, the section 220A of waveform 220 between the left side and the vertical line labeled "Begin Valsalva"). At the conclusion of this, the subject was asked to perform a Valsalva maneuver for duration of 8 seconds. See waveform section 220B between vertical lines "Begin Valsalva" and "End Valsalva" in FIG. 7. Note the progressively almost linear increase of 220B over time, ending in peak 222, and then followed by a return at 220C to baseline. Next, the device was moved to the non-patent intravenous catheter, and the same protocol was followed. See FIG. 8—note similar generally horizontal results whether before or after "Begin Valsalva"—compare 220A and 220B. This evidences proof of concept. The transduction of pressure at the sensor produces signals from which estimations of placement/patency can be based.

From the foregoing, it can be seen that the designer can create a calibration which can be stored in the processing unit 30 and which can be compared to actual measurements from an actual patient. The actual patient can and would be used to create the "baseline calibration" since each patient's intravascular or systemic venous pressures would be different. Therefore, to note patency or intraluminal placement the device will need to recognize pressure changes from that patient's baseline during the "active" (Valsalva) or "passive" (regular passive respiration) maneuvers.

In one non-limiting example, the actual patient can be asked to perform the Valsalva. The system 10 would acquire pressure measures across those similar events (pre-Valsalva, Begin Valsalva, End Valsalva) and compare to the calibration such as FIGS. 7 and 8. System 10 could be programmed to automatically decide how close or far away from the calibration of FIG. 7 to generate a signal of positive result (see 210 in FIG. 7) or negative result (see 210 in FIG. 8). As will be appreciated, the calibration and comparison can be such that identity between actual acquired waveform and a calibration waveform is required for a positive or negative result. The designer can decide what level of similarity is sufficient. Another non-limiting example is that calibration could also occur during passive respiration of the patient.

Calibration could certainly be with the same patient that is to be monitored each time. However, because identity of calibration curve and acquired waveform is not necessarily needed to be effective for estimating proper patency or placement, one calibration curve might be created and used for multiple patients. Or perhaps a limited set of calibration curves made and stored sufficient to use for a cross-section of patient populations. For example, one for each age group infant, child, adolescent, adult, and senior, and/or different height, weight, health factors, etc. It would be typical and usually preferred to use the same patient for calibration and then testing. However, a baseline "standard calibration" could be used if, e.g., unable to perform patient-specific calibration for some reason or another, or decided to create one, or a set of the same for range of possible patients.

Stage 2 of testing focused on passive pressure changes: ideal for unconscious patients, as the patient does not need to make any concerted effort. During this stage, the subject was allowed to breathe freely for 10 seconds while the recorded pressure was monitored. See FIG. 9—waveform sections 230A-230J of waveform 230. Note how it proves concept. See, for example, portion 230D which shows increasing measured pressure until peaks 240D1 and 240D2, then decreasing over portion 230E. This up to peak and then down continues with relatively similar frequency for 230F to peak 240F and then 230G; then 230H to peaks 240H1 and H2, then down 230I, and so on with 230J/peak 240J, /230K . . . . This shows normal respiratory activity, even with unconscious patients, can be measured and peaks identified indicative of correlation to proper catheter patency/placement.

The transduced pressure variation signal 230 can be mined or evaluated by appropriate programming of the processor unit to differentiate between pressure variation curves that are indicative of acceptable placement/patency of the vascular access device versus unacceptable or questionable placement/patency. For example, through a priori testing or calibration, the system could look for a pressure versus time signature like FIG. 9 to indicate a good state based on offset of peaks of the waveform versus baseline. If the curve changes to one more like FIG. 8, the programming can be set to decide the state is one of "failure" or indicative of same.

As illustrated in FIGS. 7-9, the designer could program processing unit 30 to have GUI 40 prompts, buttons, or menus to walk the user through initialization/calibration, operation, data storage, etc. See, e.g., non-limiting examples at virtual buttons 202, 204, 206, 208. And, as shown, a user-perceivable indication of status (proper or improper patency/placement) can be a part of that GUI presentation.

As will be appreciated by the foregoing, this embodiment achieves at least one or more of the aspects, features, advantages, and objects of the invention. It allows at least semi-automatic indication to a user of an vascular access device whether there is deemed proper patency and/or placement relative to a patient. This example uses sensed pressure from the intravascular probe of the vascular access device as the indirect physiological parameter to evaluate and generate the indication to the user.

E. Options and Alternatives

As will be appreciated by those of skill in this technical field and with reference to the accompanying drawings (itemized above), the invention can take many forms and embodiments. Variations obvious to those skilled in the art will be included within the invention, which is not limited by the exemplary embodiments herein.

As will be appreciated by those skilled in the art, the examples above discuss several different configurations and modes of operation. It will be apparent to those skilled in the art the following types of variations are possible using principles or aspects of the invention and are given to show the flexibility of the invention:

a. The device can be positioned adjacent to or otherwise operatively with respect to the vascular access device to measure a frequency of intravascular pressure during respiration.

b. The device can be positioned adjacent to or otherwise operatively with respect to the vascular access device, which is, positioned in the central, peripheral, arterial, or venous vasculature of the subject.

c. The device can be used whether the respiration is ventilated or non-ventilated.

d. The degree of intravascular pressure change can be the result of an active or passive respiratory activity.

e. The degree of intravascular pressure can be an active intravascular pressure.

f. Analyzed variance to generate an automatic signal can relate to: (1) a first state indicative of patency of the vascular access device or (2) a second state indicative of lack of patency of the vascular access device.

g. Patency of the vascular access device can be correlated to measuring a degree of occlusion of a previously patent vascular access device. The degree of occlusion of the previously patent vascular access device can be a thrombus.

h. Patency may be determined by detectable characteristics related to physiological changes of the continuously measured pressure waveform during passive respiration.

i. Vascular access device occlusion may be determined by a lack of detectable characteristics related to physiological changes during passive respiration.

j. Vascular access device patency can be determined during active subject respiration. For example, utilizing a breath hold after inspiration or Valsalva maneuver.

k. Vascular access device intra-luminal placement can be determined during active subject respiration. For example, utilizing a breath hold after inspiration or Valsalva maneuver.

l. Measurements can be related to physiological changes noted on waveform traces, which can be detected with respect to time.

m. Frequency of intravascular pressure change can be used as an identifiable metric to confirm intra-luminal and patent placement of a vascular access device.

n. Measurable intravascular pressure change can be used as an identifiable metric to confirm intra-luminal and patent placement of a vascular access device.

o. The technique and technology is applicable to central, peripheral, arterial and venous vasculature or any location where pressure change occurs.

p. The technique and technology can be used to detect the degree of intravascular pressure change, and frequency can differentiate placement in either the arterial or venous vascular system.

q. The technique and technology can detect the degree of intravascular pressure change, and frequency can differentiate placement in either the peripheral or central vasculature.

r. The technique and technology can detect the degree of occlusion in a previously patent catheter that is developing a thrombus by noting an upward trend in mean pressure over time.

s. Can be used as either a stand-alone device attached to a vascular catheter for intermittent monitoring or as an in-line device continuous monitoring of vascular catheter placement and patency. As will be appreciated by those skilled in this technical art, variations in the set-up of the apparatus or systems according to the invention are possible.

t. Can also be used in animals and in veterinarian contexts. As mentioned, the apparatus, system, or methods according to the invention can be used estimate patency and/or placement, including one or the other or both. This can not only measure vascular catheter patency but also appropriate vascular catheter placement intra-luminally in vasculature. For example, thrombus alone is not the only thing that can be detected; if the catheter tip is in the subcutaneous tissue outside the vessel the apparatus, system, or method will note that too as an improperly positioned/placed catheter.

u. Can be used to measure variations in intra-vascular pressure to aid in systemic cardiovascular condition diagnosis and management. As will be appreciated by those skilled in this technical area, using the apparatus, system, or methods according the invention to measure intra-vascular pressure can provide a monitoring and diagnostic tool other than simply vascular access device patency and/or placement. The non-limiting example of monitoring and evaluating cardiac function is one, as are any other states or conditions that are related to intra-vascular pressure. The apparatus, system, or method could transduce that intravascular pressure and display, record, transmit, and/or communicate it continuously or intermittently for use by the patient's medical professionals. This could assist, for example, in seeing how a patient is functioning, but also how a patient reacts to treatments, pharmaceuticals, or other treatment regimens to assist in diagnosing and/or treating patients. On a more macro-scale, if a plurality of apparatus, systems, or methods according to the invention are used with a plurality of patients, data relating to the measurements and to the conditions/treatments of patients could be collected and analyzed at a central location/computer, or a distributed set of the same. It could be mined for correlations or insights that could lead to improvements in diagnoses, care, or treatment of patients.

v. As discussed previously, it is envisioned to be more typical to establish calibration with the patient which will then be monitoring according to apparatus, systems, or methods of the invention. Creating the "baseline", reference, or calibration from the patient him/herself because each person's/patient's intravascular or systemic venous pressures are different. Thus, calibration with the patient would typically lead to better precision and accuracy in estimations of patency/placement versus not. But the invention is not limited to that paradigm. The baseline, reference, or calibration does not necessarily have to be with the patient to be monitoring/measured. Furthermore, it is to be understood that once the baseline/reference/calibration is established, it can be used in a number of ways. In one example discussed above, the Valsalva or "active" procedure can be asked of the patient to set the baseline/reference/calibration for the patient when the apparatus is in known proper patency/placement. Then, during actual use of the apparatus to monitor the patient, requesting the patient to conduct another Valsalva can be very effective to estimate, with the comparison of intravascular pressure measurements to the baseline/reference/calibration, patency and/or placement. The amplitudes of the signals indicative of intravascular pressure can be larger, and thus easier to resolve and compare. On the other hand, more "passive" conditions of the patient during calibration with known device patency and placement, can also be used to then monitor intravascular pressures during more passive respiration is also possible. The invention is not limited to any one calibration.

What is claimed is:

1. An apparatus for automatic estimation of proper patency and placement of an intravascular lumen of a vascular access device in a patient, the apparatus configured for attachment to a proximal end of the vascular access device disposed outside of the patient in use, the apparatus comprising:
  a. a sensor comprising:
    i. a mounting end configured to sealingly mount the sensor to the proximal end of the vascular access device; and
    ii. a sensing element responsive to variations in pressure from fluid or gas phase substances in the intravascular lumen of the vascular access device, the sensing element producing an electrical signal comprising one or more measurements of pressure in the intravascular lumen of the vascular access device; and
  b. a circuit operably connected to the sensor, the circuit configured to:
    i. acquire and quantify the one or more measurements of pressure in the intravascular lumen resulting in one or more quantified measurements;
    ii. compare the one or more quantified measurements to a reference or calibration of a physiological parameter to produce variations in pressure in the intravascular lumen of the vascular access device to indicate a status of patency or placement of the vascular access device in the patient; and
    iii. generate a signal based on the status of patency or placement of the vascular access device in the patient that outputs in user-perceivable form.

2. The apparatus of claim 1, wherein the physiological parameter comprises intravascular pressure during respiration of a human or animal.

3. The apparatus of claim 1, wherein the sensor comprises a load cell exposed directly or indirectly to pressure in the intravascular lumen.

4. The apparatus of claim 3, wherein the load cell is either:
  a. at or integrated with the vascular access device;
  b. spaced from the vascular access device.

5. The apparatus of claim 4, wherein the load cell produces in analog form the quantified measurements, and the circuit converts the analog form to digital form for processing by a microprocessor.

6. The apparatus of claim 5, wherein the microprocessor is programmed to compare the digital form of the quantified measurements with a reference or calibration of a time-based waveform indicative of pressure variations over time of intravascular pressure during respiration of the intravascular lumen of the vascular access device indicative of proper patency or placement.

7. The apparatus of claim 6, wherein the reference or calibration is based on at least one of:
  a. central, peripheral, arterial, or venous vasculature of the patient;
  b. ventilated respiration;
  c. non-ventilated respiration;
  d. active respiratory activity; or
  e. passive respiratory activity.

8. The apparatus of claim 1, wherein the signal comprises a user-perceivable alarm or indication.

9. The apparatus of claim 8, wherein the user-perceivable alarm or indication comprises:
  a. a light,
  b. an audible buzzer,
  c. a vibration,
  d. readable displayed text or graphics, or
  e. some combination of the same.

10. A system comprising the apparatus of claim 1 in combination with a processing unit comprising:
  i. a microprocessor;
  ii. a transducer of the sensed parameter into a digital signal useable by the microprocessor;
  iii. on-board digital storage; and
  iv. on-board communication output.

11. A kit comprising pre-selected components of the system of claim 10, wherein the kit is packaged for use by a health care professional.

* * * * *